(12) United States Patent
Danielescu et al.

(10) Patent No.: US 12,144,902 B2
(45) Date of Patent: Nov. 19, 2024

(54) SELF-CLEANING DEVICE

(71) Applicant: Accenture Global Solutions Limited, Dublin (IE)

(72) Inventors: Lavinia Andreea Danielescu, San Francisco, CA (US); Aditi Maheshwari, San Francisco, CA (US); Mark Benjamin Greenspan, San Francisco, CA (US)

(73) Assignee: Accenture Global Solutions Limited, Dublin (IE)

( * ) Notice: Subject to any disclaimer, the term of this patent is extended or adjusted under 35 U.S.C. 154(b) by 202 days.

(21) Appl. No.: 17/335,344

(22) Filed: Jun. 1, 2021

(65) Prior Publication Data

US 2021/0369883 A1    Dec. 2, 2021

Related U.S. Application Data

(60) Provisional application No. 63/032,979, filed on Jun. 1, 2020.

(51) Int. Cl.
*A61L 2/08* (2006.01)
*A61L 2/10* (2006.01)
(Continued)

(52) U.S. Cl.
CPC ............... *A61L 2/088* (2013.01); *A61L 2/10* (2013.01); *A61L 2/24* (2013.01); *A61L 2101/12* (2020.08);
(Continued)

(58) Field of Classification Search
CPC ... A61L 2/088; A61L 2/10; A61L 2/24; A61L 2101/28; A61L 2101/12; A61L 2202/13; A61L 2202/14; A61L 2202/26; A61L 2/00; A61L 9/00; A61L 9/205; A61L 2209/111; B01D 61/22; B01D 71/024; B01D 2325/43; B01D 2325/44; B01D 2325/40;
(Continued)

(56) References Cited

U.S. PATENT DOCUMENTS 4,045,174 A    8/1977    Fuhring et al.
5,942,007 A    8/1999    Berndt et al.
(Continued)

FOREIGN PATENT DOCUMENTS

DE    10124457    12/2002
WO    WO 2017/030851    2/2017

OTHER PUBLICATIONS

3M, "Product Data Sheet: 3M™ Conductive Film Products," dated 2014, 3 pages.
(Continued)

*Primary Examiner* — Xiuyu Tai
(74) *Attorney, Agent, or Firm* — Polsinelli PC

(57) ABSTRACT

This document describes self-cleaning devices. In one aspect, a self-cleaning device includes a fabric having a surface covered with a photocatalyst, one or more light sources embedded in the fabric, and a triggering mechanism that activates a cleaning cycle by activating the one or more light sources. The triggering mechanism can include a pressure sensor. The triggering mechanism can be configured to activate the cleaning cycle in response to detecting a decrease in pressure being applied to the pressure sensor.

24 Claims, 9 Drawing Sheets

(51) Int. Cl.
  *A61L 2/24* (2006.01)
  *A61L 101/12* (2006.01)
  *A61L 101/28* (2006.01)
(52) U.S. Cl.
  CPC ....... *A61L 2101/28* (2020.08); *A61L 2202/13* (2013.01); *A61L 2202/14* (2013.01); *A61L 2202/26* (2013.01)
(58) Field of Classification Search
  CPC .... C02F 1/30; C02F 1/725; C02F 1/32; C02F 2101/322; C02F 2201/3224; C02F 2209/40; C02F 2305/10; A47C 7/72; A47C 7/725; A47C 31/00; A47C 7/56; A47C 7/62; B08B 7/0057; B08B 7/0035
  See application file for complete search history.

(56) References Cited

U.S. PATENT DOCUMENTS

| | | | |
|---|---|---|---|
| 9,694,739 B2 | 7/2017 | Salter et al. | |
| 2010/0029157 A1* | 2/2010 | Brochier | C03C 25/47 442/187 |
| 2014/0286843 A1* | 9/2014 | Grossman | C02F 1/725 422/186 |
| 2015/0147229 A1* | 5/2015 | Fewkes | G02B 6/0066 422/186.3 |
| 2015/0273093 A1* | 10/2015 | Holub | B60Q 3/68 250/492.1 |
| 2016/0074547 A1* | 3/2016 | Dobrinsky | A43B 17/10 250/492.1 |
| 2016/0129432 A1* | 5/2016 | Ozaki | B01J 23/72 502/309 |
| 2018/0325454 A1* | 11/2018 | Petelenz | A61F 2/76 |
| 2020/0061223 A1 | 2/2020 | Hallack | |

OTHER PUBLICATIONS

Adafruit.com [online], "Firewalker LED Sneakers: Make Velostat Step Sensors," available on or before Sep. 2, 2013, via Internet Archive: Wayback Machine URL<https://web.archive.org/web/20130902032148/https://learn.adafruit.com/firewalker-led-sneakers/make-velostat-step-sensors>, retrieved on Jan. 3, 2022, retrieved from URL<https://learn.adafruit.com/firewalker-led-sneakers/make-velostat-step-sensors>, 16 pages.

Adafruit.com [online], "Firewalker LED Sneakers: Overview," available on or before Sep. 2, 2013, via Internet Archive: Wayback Machine URL<https://web.archive.org/web/20130902014917/https://learn.adafruit.com/firewalker-led-sneakers>, retrieved on Jan. 3, 2022. retrieved from URL<https://learn.adafruit.com/firewalker-led-sneakers>, 18 pages.

Adafruit.com [online], "Pressure-Sensitive Conductive Sheet (Velostat/Linqstat)," available on or before Jul. 7, 2013, via Internet Archive: Wayback Machine URL<https://web.archive.org/web/20130707074043/https://www.adafruit.com/product/1361>, retrieved on Jan. 3, 2022, retrieved from URL<https://www.adafruit.com/product/1361>, 7 pages.

Arion.run [online], "ARION wearable," available on or before Aug. 5, 2020 via Internet Archive: Wayback Machine URL<https://web.archive.org/web/20200805223715/https://www.arion.run/wearable/>, retrieved on Oct. 8, 2021, retrieved from URL<https://www.arion.run/wearable/>, 11 pages.

EP Extended Search Report in European Appln. No. 21177211.6, dated Oct. 27, 2021, 8 pages.

Genengnew.com [online], "UV Light That Is Safe for Humans but Bad for Bacteria and Viruses," dated Feb. 9, 2018, retrieved on Oct. 18, 20201, retrieved from URL<https://www.genengnews.com/topics/translational-medicine/uv-light-that-is-safe-for-humans-but-bad-for-bacteria-and-viruses/>, 3 pages.

GetCarv.com [online], "CARV: How it Works," available on or before Oct. 22, 2020, via Internet Archive: Wayback Machine URL<https://web.archive.org/web/20201022004905/https://getcarv.com/how-it-works>, retrieved on Jan. 3, 2022, retrieved from URL<https://getcarv.com/how-it-works>, 16 pages.

Kobakant.at [online], "Conductive Materials: Velostat," available on or before Jun. 5, 2011, via Internet Archive: Wayback Machine URL<https://web.archive.org/web/20110605153425/https://www.kobakant.at/DIY/?p=381>, retrieved on Jan. 3, 2022, retrieved from URL<https://www.kobakant.at/DIY/?p=381>, 7 pages.

Lowe et al., "N95 Filtering Facepiece Respirator Ultraviolet Germicidal Irradiation (UVGI) Process for Decontamination and Reuse," Nebraska Medicine, Apr. 10, 2020, 19 pages.

MedGadget.com [online], "Reusable Textiles to Repel Viruses," dated May 14, 2020, retrieved on Oct. 18, 2021, retrieved from URL<https://www.medgadget.com/2020/05/reusable-textile-to-repel-viruses.html>, 3 pages.

Rein et al., "Diode fibres for fabric-based optical communications," Nature, Aug. 8, 2018, 560(7717):214-218.

SensoriaFitness.com [online], "Sensoria Artificial Intelligence Sportswear," available on or before Jun. 27, 2013 via Internet Archive: Wayback Machine URL<https://web.archive.org/web/20130627164235/https://www.sensoriafitness.com/>, retrieved on Oct. 8, 2021, retrieved from URL<https://www.sensoriafitness.com/>, 10 pages.

SkarredGhost.com [online], "Cleanbox Technology kills coronavirus on your VR headset," dated Apr. 30, 2020, retrieved on Oct. 18, 2021, retrieved from URL<https://skarredghost.com/2020/04/30/cleanbox-coronavirus-vr-lbvr/>, 11 pages.

Tekscan.com [online], "F-Scan System," available on or before Feb. 2, 2016 via Internet Archive: Wayback Machine URL:https://web.archive.org/web/20160202032836/https://www.tekscan.com/products-solutions/systems/f-scan-system>, retrieved on Oct. 8, 2021, retrieved from URL:https://www.tekscan.com/products-solutions/systems/f-scan-system>, 5 pages.

Welch et al., "Far-UVC light: A new tool to control the spread of airborne-mediated microbial diseases," Sci. Reports, Feb. 9, 2018, 8:2752, 7 pages.

Zahid et al., "Fabrication of Visible Light-Induced Antibacterial and Self-Cleaning Cotton Fabrics Using Manganese Doped $TiO_2$ Nanoparticles," ACS Appl. Bio Materials, Sep. 7, 2018, 1(4):1154-1164.

Adafruit.com [online], "Adafruit LED Sequins—Warm White—Pack of 5," available on or before Jul. 21, 2014 via Internet Archive: Wayback Machine URL<https://web.archive.org/web/20140721211011/https://www.adafruit.com/produ ct/1758>, retrieved on Apr. 25, 2022, retrieved from URL<https://www.adafruit.com/product/1758>, 6 pages.

Adafruit.com [online], "Adafruit METRO 328—Arduino Compatible—with Headers—ATmega328," available on or before May 15, 2015 via Internet Archive: Wayback Machine URL<https://web.archive.org/web/20150515053508/https://www.adafruit.com/produ ct/2488>, retrieved on Apr. 25, 2022, retrieved from URL<https://www.adafruit.com/product/2488>, 9 pages.

AdaFruit.com [online], "Conductive Thread: Stitching around circuit boards," Jan. 2, 2013, retrieved on Apr. 26, 2022, retrieved from URL<https://learn.adafruit.com/conductive-thread/stitching-around-circuit-boards>, 20 pages.

Akinrotoye et al., "Occurrence of Pathogenic bacteria on public surfaces within community schools in Abeokuta Environs, Ogun State," J. Environ. Treat. Techniques, Oct. 2018, 6(3):47-52.

Alistar et al., "Semina Aeternitatis: Using Bacteria for Tangible Interaction with Data," Presented at Proceedings of the 2020 CHI Conference on Human Factors in Computing Systems, Honolulu, Hi, USA, Apr. 25-30, 2020; Extended Abstracts of the 2020 CHI Conference on Human Factors in Computing Systems, Apr. 2020, 13 pages.

Amazon.com [online], "BTMETER," upon information and belief, available No. later than Aug. 12, 2020, retrieved on Apr. 25, 2022, retrieved from URL<https://www.amazon.com/stores/BTMETER/page/0BCF3C8A-52A3-4F3D-9322-154B2676C255?ref_-ast_bln>, 9 pages.

Amazon.com [online], "Jukstg-US: Results," upon information and belief, available no later than Aug. 12, 2020, retrieved on Apr. 25, 2022, retrieved from URL<https://www.amazon.com/s?me=A3MBN10QH431NJ&marketplaceID=ATVPDKIKXODER>, 3 pages.

(56) References Cited

OTHER PUBLICATIONS

Amazon.com [online], "Neewer 12×5 feet/3.6×1.5 meters Polyester White Seamless Diffusion Fabric for Photography Softbox, Light Tent and DIY Lighting Modifier," Mar. 22, 2017, retrieved on Apr. 22, 2022, retrieved from URL<https://www.amazon.com/Neewer-Seamless-Diffusion-Photography-Lighting/dp/B06XSBDWXX/ref=sr_1_3?dchild-1&keywords-camera+light+diffusing+fabric&qid=1622075021&sr=8-3>, 6 pages.

Amazon.com [online], "VIVOSUN Highly Reflective Mylar Film Roll 4FT×50FT for Outdoor Grow Room Indoor Decoration Aluminum Paint Coated 2 Mil Sliver," upon information and belief, available no later than Jun. 3, 2017, retrieved on Apr. 22, 2022, retrieved from URL<https://www.amazon.com/VIVOSUN-Horticulture-Highly-Reflective-Mylar/dp/B018VI76JA/ref=asc_df_B018VI76JA/?tag-hyprod-20&linkCode=df0&hvadid=167150018785&hvpos=&hvnetw=g&hvrand=44356728 64214242547&hvpone-&hvptwo=&hvqmt-&hvdev-c&hvdvcmdl=&hvlocint-&hvl ocphy=9032054&hvtargid=pla-309671299140&psc=1>, 11 pages.

Bell et al., "Self-deStaining Textiles: Designing Interactive Systems with Fabric, Stains and Light," Presented at Proceedings of the 2021 CHI Conference on Human Factors in Computing Systems, Yokohama, Japan, May 8-13, 2021, 12 pages.

Berzowska et al., "Memory Rich Garments: Body-Based Displays," Presented at Proceedings of the Special Interest Group on Computer Graphics and Interactive Techniques Conference, Los Angeles, CA, USA, Aug. 1-4, 2005; ACM SIGGRAPH 2005 Electronic Art and Animation Catalog, Aug. 2005, 168-171.

Berzowska et al., "SMOKS: The Memory Suits," Presented at Proceedings of the CHI 2006 Conference on Human Factors in Computing Systems, Montreal, Quebec, Canada, Apr. 22-27, 2006; CHI '06 Extended Abstracts on Human Factors in Computing Systems, Apr. 2006, 538-543.

Berzowska, "Very Slowly Animating Textiles: Shimmering Flower," Presented at Proceedings of the 31st Annual Conference on Computer Graphics and Interactive Techniques, Los Angeles, Ca, USA, Aug. 8-12, 2004; Acm Siggraph 2004 Sketches, Aug. 2004, 1 page.

Bozzi et al., "Self-cleaning of wool-polyamide and polyester textiles by TiO2-rutile modification under daylight irradiation at ambient temperature," J. Photochem. Photobiol. A: Chemistry, May 15, 2005, 172(1):27-34.

CDC.gov [online], "Cleaning, Disinfection, and Hand Hygiene in Schools—a Toolkit for School Administrators," available on or before Aug. 9, 2020 via Internet Archive: Wayback Machine URL<https://web.archive.org/web/20200809065545/https://www.cdc.gov/coronaviru s/2019-ncov/community/schools-childcare/clean-disinfect-hygiene.html>, retrieved on Apr. 25, 2022, retrieved from URL<https://www.cdc.gov/coronavirus/2019-ncov/community/schools-childcare/clean-disinfect-hygiene.html>, 9 pages.

Chan et al., "Data Storage and Interaction using Magnetized Fabric," Presented at Proceedings of the 30th Annual ACM Symposium on User Interface Software and Technology, Quebec City, Quebec, Canada, Oct. 22-25, 2017; UIST '17: Proceedings of the 30th Annual ACM Symposium on User Interface Software and Technology, Oct. 2017, 655-663.

ChemicalSafetyFacts.org [online], "Titanium Dioxide," available on or before Aug. 30, 2014 via Internet Archive: Wayback Machine URL<https://web.archive.org/web/20140830003026/https://www.chemicalsafetyfacts.org/titanium-dioxide/?tab=1>, retrieved on Apr. 26, 2022, retrieved from URL<https://www.chemicalsafetyfacts.org/titanium-dioxide/>, 4 pages.

CNet.com [online], "UV light and the coronavirus: Big Ass Fans might have a solution," Aug. 8, 2020, retrieved on Apr. 26, 2022, retrieved from URL<https://www.cnet.com/home/smart-home/uv-light-and-the-coronavirus-big-ass-fans-might-have-a-solution-haiku-uvc-covid-19/>, 5 pages.

CNet.com [online], "UVC wands kill viruses. Experts warn they're also a 'major safety issue'," Oct. 20, 2020, retrieved on Apr. 26, 2022, retrieved from URL<https://www.cnet.com/home/smart-home/uvc-light-wands-kill-viruses-experts-warn-major-safety-issue-coronavirus-covid-19/>, 7 pages.

ColorMuse.io [online], "Color Muse RGB Meter Instrument: Variable Inc.," available on or before Oct. 14, 2017 via Internet Archive: Wayback Machine URL<https://web.archive.org/web/20171014102145/https://colormuse.io/>, retrieved on Apr. 25, 2022, retrieved from URL<https://colormuse.io/>, 10 pages.

CostCo.com [online], "Kirkland Signature," available on or before Jun. 10, 2014 via Internet Archive: Wayback Machine URL<https://web.archive.org/web/20140610184126/https://www.costco.com/kirkland-signature.html>, retrieved on Apr. 25, 2022, retrieved from URL<https://www.costco.com/kirkland-signature.html>, 2 pages.

Coupang.com [online], "25 kinds of leftover top quality cotton 20 count plain fabric," upon information and belief, available No. later than Sep. 16, 2020, retrieved on Apr. 25, 2022, retrieved from URL<https://www.coupang.com/vp/products/282044747?vendorItemId=5249553408 &isAddedCart=>, 10 pages (with English translation).

Craft of Use: Post-Growth Fashion, 1st ed., Fletcher, Apr. 27, 2016, 304 pages.

DesignNews.com [online], "COVID-19 Giving Touchless Interfaces a Chance to Make an Impression," Jun. 3, 2020, retrieved on Apr. 25, 2022, retrieved from URL<https://www.designnews.com/design-hardware-software/covid-19-giving-touchless-interfaces-chance-make-impression-0>, 8 pages.

Devendorf et al., ""I don't Want to Wear a Screen": Probing Perceptions of and Possibilities for Dynamic Displays on Clothing," Presented at Proceedings of the 2016 CHI Conference on Human Factors in Computing Systems, San Jose, CA, USA, May 7-12, 2016; CHI '16: Proceedings of the 2016 CHI Conference on Human Factors in Computing Systems, May 2016, 6028-6039.

Devendorf et al., "Adapting Double Weaving and Yarn Plying Techniques for Smart Textiles Applications," Presented at Proceedings of the Thirteenth International Conference on Tangible, Embedded, and Embodied Interaction, Tempe, AZ, USA, Mar. 17-20, 2019; TEI '19: Proceedings of the Thirteenth International Conference on Tangible, Embedded, and Embodied Interaction, Mar. 2019, 77-85.

DharmaTrading.com [online], "Batik Basics with Fiber Reactive Dyes," available on or before Oct. 1, 2013 via Internet Archive: Wayback Machine URL<https://web.archive.org/web/20131001180515/https://www.dharmatrading.com/techniques/batik-instructions.html>, retrieved on Apr. 25, 2022, retrieved from URL<https://www.dharmatrading.com/techniques/batik-instructions.html>, 6 pages.

DIYBIO.org [online], "Diy Bio: An Institution for the Do-It-Yourself Biologist," available on or before Jan. 2, 2019 via Internet Archive: Wayback Machine URL<https://web.archive.org/web/20190102155832/https://diybio.org/>, retrieved on Apr. 25, 2022, retrieved from URL<https://diybio.org/>, 3 pages.

Drexel.edu [online], "Smart Fabric Bellyband," available on or before Aug. 20, 2018 via Internet Archive: Wayback Machine URL<https://web.archive.org/web/20180820041410/https://drexel.edu/functional-fabrics/research/projects/smart-fabric-bellyband>, retrieved on Apr. 26, 2022, retrieved from URL<https://drexel.edu/functional-fabrics/research/projects/smart-fabric-bellyband/>, 3 pages.

Elcott, "Into the dark chamber: Avant-garde photograms and the cinematic imaginary," Dissertation for the degree of Doctor of Philosophy, Princeton University, Jan. 2009, 338 pages.

Emami et al., "Self-cleaning Properties of Nylon 6 Fabrics Treated with Corona and TiO2 Nanoparticles under Both Ultraviolet and Daylight Irradiations," Fibers and Polymers, Jun. 25, 2018, 19(5):1014-1023.

Fazli et al., "A novel chitosan-polyethylene oxide nanofibrous mat designed for controlled co-release of hydrocortisone and imipenem/cilastatin drugs," Int. J. Pharmaceuticals, Nov. 20, 2016, 513(1-2):636-647.

Fazli et al., "Controlled release of cefazolin sodium antibiotic drug from electrospun chitosan-polyethylene oxide nanofibrous Mats," Mater. Sci. Eng. C Mater. Biol. Applications, Feb. 1, 2017, 71:641-652.

Foster et al., "Photocatalytic disinfection using titanium dioxide: spectrum and mechanism of antimicrobial activity," Appl. Microbiol. Biotechnology, Jun. 2011, 90(6):1847-1868.

(56) References Cited

OTHER PUBLICATIONS

Garg et al., "Improvement of adhesion of conductive polypyrrole coating on wool and polyester fabrics using atmospheric plasma treatment," Synth. Metals, Jan. 15, 2007, 157(1):41-47.

Gashti et al., "Characterization of nanocomposite coatings on textiles: a brief review on Microscopic technology," Curr. Microscop. Contribut. Adv. Sci. Technology, 2012, 2:1424-1437.

Golgouneh et al., "A Comparative Feasibility Analysis for Sensing Swelling with Textile-based Soft Strain Sensors," Presented at Proceedings of the 23rd International Symposium on Wearable Computers, London, UK, Sep. 9-13, 2019; ISWC '19: Proceedings of the 23rd International Symposium on Wearable Computers, Sep. 2019, 60-65.

Hallnäs et al., "Textile displays: using textiles to investigate computational technology as design material," Presented at Proceedings of the Second Nordic Conference on Human-Computer Interaction, Aarhus, Denmark, Oct. 19-23, 2002; NordiCHI '02: Proceedings of the Second Nordic Conference on Human- Computer Interaction, October 202, 157-166.

Harwood et al., "Shedding Light on Retail Environments," Presented at Proceedings of the 2013 Conference on Eye Tracking South Africa, Cape Town, South Africa, Aug. 29-31, 2013; ETSA '13: Proceedings of the 2013 Conference on Eye Tracking South Africa, Aug. 2013, 2-7.

Hassan, "Enhanced Antistatic and Mechanical Properties of Corona Plasma Treated Wool Fabrics Treated with 2,3-Epoxypropyltrimethylammonium Chloride," Ind. Eng. Chem. Research, Jun. 13, 2014, 53(27):10954-10964.

Honeywell.com [online], "Honeywell UV Treatment System," available on or before Aug. 3, 2020 via Internet Archive: Wayback Machine URL<https://web.archive.org/web/20200803031822/https://aerospace.honeywell.com /en/learn/products/cabin/uv-cabin-system>, retrieved from Apr. 25, 2022, retrieved from URL<https://aerospace.honeywell.com/us/en/learn/products/cabin/uv-treatment-system>, 2 pages.

Honnet et al., "PolySense: Augmenting Textiles with Electrical Functionality using In-Situ Polymerization," Presented at Proceedings of the 2020 CHI Conference on Human Factors in Computing Systems, Honolulu, Hi, USA, Apr. 25-30, 2020; CHI '20: Proceedings of the 2020 CHI Conference on Human Factors in Computing Systems, Apr. 2020, 1-13.

IndustrialPrintMagazine.com [online], "A Strong Hold: Surface Treatments-Corona, Flame, and Plasma," Apr. 2019, retrieved on Apr. 22, 2022, retrieved from URL<https://industrialprintmagazine.com/a-strong-hold/>, 3 pages.

IndustrialPrintMagazine.com [online], "Treatment Options: Equipment for Enhanced Adhesion," Apr. 2019, retrieved on Apr. 22, 2022, retrieved from URL<https://industrialprintmagazine.com/treatment-options/>, 2 pages.

Jin et al., "Photo-Chromeleon: Re-Programmable Multi-Color Textures Using Photochromic Dyes," Presented at Proceedings of Acm Siggraph 2020 Emerging Technologies, Virtual Event, USA, Aug. 17, 2020; SIGGRAPH '20: Acm Siggraph 2020 Emerging Technologies, Aug. 2020, 7:1-2.

Kan et al., "Social Textiles: Social Affordances and Icebreaking Interactions Through Wearable Social Messaging," Presented at Proceedings of the Ninth International Conference on Tangible, Embedded, and Embodied Interaction, Stanford, Ca, USA, Jan. 15-19, 2015; TEI '15: Proceedings of the Ninth International Conference on Tangible, Embedded, and Embodied Interaction, Jan. 2015, 619-624.

Kan et al., "Textile Modification with Plasma Treatment," RJTA, Feb. 2006, 10(1):49-64.

Khataee et al., "Self-cleaning acrylic water-based white paint modified with different types of TiO2 nanoparticles," Pigment Resin Technology, Jan. 2016, 45(1)24-29.

Kim et al., "Reliable Actual Fabric-Based Organic Light-Emitting Diodes: Toward a Wearable Display," Adv. Electr. Materials, Nov. 2016, 2(11): 1600220, 7 pages.

Kim et al., "Surface morphology of polyethylene after treatment in a corona discharge," J. Appl. Polym. Science, Jun. 1971, 15(6): 1357-1364.

Kobakant.at [online], "The Crying Dress," 2012, retrieved on Apr. 26, 2022, retrieved from URL<https://www.kobakant.at/?p=222>, 5 pages.

Kohsari et al., "Antibacterial electrospun chitosan-polyethylene oxide nanocomposite mats containing bioactive silver nanoparticles," Carbohydr. Polymers, Apr. 20, 2016, 140:287-298.

Kohsari et al., "Antibacterial electrospun chitosan-polyethylene oxide nanocomposite mats containing ZIF-8 nanoparticles," Int. J. Biol. Macromolecules, Oct. 2016, 91:778-788.

Koncar, "Optical Fiber Fabric Displays," Opt. Photonics News, Apr. 2005, 16(4):40-44.

Kowal et al., "Biocidal effect and durability of nano-TiO2 coated textiles to combat hospital acquired infections," RSC Advances, Apr. 16, 2014, 4(38): 19945-19952.

Kubacka et al., "Boosting TiO2-anatase antimicrobial activity: Polymer-oxide thin films," Appl. Catal. B Environmental, Jul. 15, 2009, 89(3-4):441-447.

Kuznetsov et al., "DIYbio Things: Open Source Biology Tools as Platforms for Hybrid Knowledge Production and Scientific Participation," Presented at Proceedings of the 33rd Annual ACM Conference on Human Factors in Computing Systems, Seoul, Republic of Korea, Apr. 18-23, 2015; CHI '15: Proceedings of the 33rd Annual ACM Conference on Human Factors in Computing Systems, Apr. 2015, 4065-4068.

Lee et al., "Patina Engraver: Visualizing Activity Logs as Patina in Fashionable Trackers," Presented at Proceedings of the 33rd Annual ACM Conference on Human Factors in Computing Systems, Seoul, Republic of Korea, Apr. 18-23, 2015; CHI '15: Proceedings of the 33rd Annual ACM Conference on Human Factors in Computing Systems, Apr. 2015, 1173-1182.

Li et al., "Creation of self-cleaning polyester fabric with TiO2 nanoparticles via a simple exhaustion process: Conditions optimization and stain decomposition pathway," Mat. Design, Feb. 15, 2018, 140:366-375.

Liston et al., "Plasma surface modification of polymers for improved adhesion: a critical review," J. Adhes. Sci. Technology, 1993, 7(10):1091-1127.

LivingColour.eu [online], "Living Colour," available on or before Dec. 8, 2018 via Internet Archive: Wayback Machine URL<https://web.archive.org/web/20181208134842/https://livingcolour.eu/>, retrieved on Apr. 25, 2022, retrieved from URL<https://livingcolour.eu/>, 8 pages.

Luttrell et al., "Why is anatase a better photocatalyst than rutile? - Model studies on epitaxial TiO2 films," Sci. Reports, Feb. 10, 2014, 4:4043, 8 pages.

Mahdich et al., "A new method for in situ synthesis of Ag-TiO2 nanocomposite particles on polyester/cellulose fabric by photoreduction and self-cleaning properties," Cellulose, Feb. 14, 2018, 25:2355-2366.

Makezine.com [online], "How-To: Rust-Oleum NeverWet Sidewalk Art," Sep. 30, 2013, retrieved on Apr. 25, 2022, retrieved from URL<https://makezine.com/2013/09/30/how-to-rust-oleum-neverwet-sidewalk-art/>, 6 pages.

MasterBond.com [online], "Typical Coating Techniques," available on or before Apr. 18, 2021 via Internet Archive: Wayback Machine URL<https://web.archive.org/web/20210418030040/https://www.masterbond.com/applications/typical-coating-techniques>, retrieved on Apr. 22, 2022, retrieved from URL<https://www.masterbond.com/applications/typical-coating-techniques>, 2 pages.

Meilert et al., "Photocatalytic self-cleaning of modified cotton textiles by TiO2 clusters attached by chemical spacers," J. Mol. Catal. A Chemical, Aug. 2, 2005, 237(1-2): 101-108.

Mejía et al., "Self-cleaning modified TiO2-cotton pretreated by UVC-light (185 nm) and RF-plasma in vacuum and also under atmospheric pressure," Appl. Catal. B Environmental, Sep. 7, 2009, 91(1-2):481-488.

Merritt et al., "Living media interfaces: a multi-perspective analysis of biological materials for interaction," Digital Creativity, Jan. 21, 2020, 31(1):1-21.

(56) References Cited

OTHER PUBLICATIONS

Michelitsch et al., "Haptic chameleon: a new concept of shape-changing user interface controls with force feedback," Presented at Proceedings of CHI 2004 Conference on Human Factors in Computing Systems, Vienna, Austria, Apr. 24-29, 2004; Chi Ea '04: CHI '04 Extended Abstracts on Human Factors in Computing Systems, Apr. 2004, 1305-1308.
Mikkonen et al., "Frequency-based design of smart textiles," Presented at Proceedings of the 2019 CHI Conference on Human Factors in Computing Systems, Glasgow, Scotland, UK, May 4-9, 2019; CHI '19: Proceedings of the 2019 CHI Conference on Human Factors in Computing Systems, May 2019, 12 pages.
Mishra et al., "Deposition of Ag doped $TiO_2$ on cotton fabric for wash durable UV protective and antibacterial properties at very low silver concentration," Cellulose, Jun. 3, 2017, 24(8):3555-3571.
Mishra et al., "Silver-Doped $TiO_2$-Coated Cotton Fabric as an Effective Photocatalytic System for Dye Decolorization in UV and Visible Light," Photochem. Photobiology, Mar. 2019, 95(2):522-531.
MIT.edu [online], "fibers@mit," available on or before Aug. 6, 2019 via Internet Archive: Wayback Machine URL<https://web.archive.org/web/20190806224830/http://mit-pbg.mit.edu/>, retrieved on Apr. 22, 2022, retrieved from URL<http://mit-pbg.mit.edu/>, 2 pages.
MIT.edu [online], "Wearable Sanitizer: Open-source, On-body Sanitizer," available on or before Apr. 7, 2020 via Internet Archive: Wayback Machine URL<https://web.archive.org/web/20200407225629/https://www.media.mit.edu/projects/wearable-sanitizer/overview/>, retrieved on Apr. 26, 2022, retrieved from URL<https://www.media.mit.edu/projects/wearable-sanitizer/overview/>, 4 pages.
Molenaar et al., "Light and the Perception of Cleanliness in Public Spaces," J. Man Machine Technology, Jun. 2013, 2(1):63-70.
Nazari et al., "Nano $TiO_2$ photo-catalyst and sodium hypophosphite for cross-linking cotton with poly carboxylic acids under UV and high temperature," Appl. Catal. A General, Dec. 15, 2009, 371(1-2):10-16.
Odom et al., "Attending to Slowness and Temporality with Olly and Slow Game: A Design Inquiry Into Supporting Longer-Term Relations with Everyday Computational Objects," Presented at Proceedings of the 2018 CHI Conference on Human Factors in Computing Systems, Montreal, Quebec, Canada, Apr. 21-26, 2018; CHI '18: Proceedings of the 2018 CHI Conference on Human Factors in Computing Systems, Apr. 2018, 13 pages.
Orth et al., "Fabric Computing Interfaces," Presented at Proceedings of the ACM Conference on Human Factors and Computing Systems, Los Angeles, CA, USA, Apr. 18-23, 1998; CHI '98: CHI 98 Conference Summary on Human Factors in Computing Systems, Apr. 1998, 331-332.
Pataranutaporn et al., "Living Bits: Opportunities and Challenges for Integrating Living Microorganisms in Human-Computer Interaction," Presented at Proceedings of the Augmented Humans International Conference, Kaiserslautern, Germany, Mar. 16-17, 2020; AHs '20: Proceedings of the Augmented Humans International Conference, Mar. 2020, 12 pages.
Paz et al., "Photooxidative self-cleaning transparent titanium dioxide films on glass," J. Mater. Research, Mar. 3, 2011, 10:2842-2848.
Peiris et al., "dMarkers: ubiquitous dynamic makers for augmented reality," Presented at Proceedings of the 10th International Conference on Virtual Reality Continuum and Its Applications in Industry, Hong Kong, China, Dec. 11-12, 2011; VRCAI '11: Proceedings of the 10th International Conference on Virtual Reality Continuum and Its Applications in Industry, Dec. 2011, 217-224.
Pichat et al., "Purification/deodorization of indoor air and gaseous effluents by $TiO_2$ photocatalysis," Catal. Today, Dec. 25, 2000, 63(2-4):363-369.
Pomoni et al., "Thermal treatment and environment effect on transient photoconductivity behavior of anatase $TiO_2$ with dominant $\{0\ 0\ 1\}$ facets," J. Alloy. Compounds, May 5, 2013, 558:1-5.
Post et al., "E-broidery: Design and fabrication of textile-based computing," IBM Syst. Journal, 2000, 39(3.4):840-860.
Poupyrev et al., "Project Jacquard: Interactive Digital Textiles at Scale," Presented at Proceedings of the 2016 CHI Conference on Human Factors in Computing Systems, San Jose, Ca, USA, May 7-12, 2016; CHI '16: Proceedings of the 2016 CHI Conference on Human Factors in Computing Systems, May 2016, 4216-4227.
ProLampSales.com [online], "Far UVC (222nm) Ultraviolet Germicidal," available on or before Sep. 26, 2020 via Internet Archive: Wayback Machine URL<https://web.archive.org/web/20200926111115/https://www.prolampsales.com/pages/far-uvc-222nm-ultraviolet-germicidal>, retrieved on Apr. 25, 2022, retrieved from URL<https://www.prolampsales.com/pages/far-uvc-222nm-ultraviolet-germicidal>, 9 pages.
Qamar et al., "HCI meets Material Science: A Literature Review of Morphing Materials for the Design of Shape-Changing Interfaces," Presented at Proceedings of the 2018 CHI Conference on Human Factors in Computing Systems, Montreal, Quebec, Canada, Apr. 21-26, 2018; CHI '18: Proceedings of the 2018 CHI Conference on Human Factors in Computing Systems, Apr. 2018, 23 pages.
Qi et al., "Functionalizing Polyester Fiber with a Self-Cleaning Property Using Anatase $TiO_2$ and Low-Temperature Plasma Treatment," Int. J. Appl. Ceram. Technology, Dec. 2007, 4(6):554-563.
Robles et al., "Texturing the" material turn" in interaction design," Presented at Proceedings of the Fourth International Conference on Tangible, Embedded, and Embodied Interaction, Cambridge, Ma, USA, Jan. 24-27, 2010; TEI '10: Proceedings of the Fourth International Conference on Tangible, Embedded, and Embodied Interaction, Jan. 2010, 137-144.
Senić et al., "Application of $TiO_2$ Nanoparticles for Obtaining Self-Decontaminating Smart Textiles," Sci. Technic. Review, 2011, 61(3-4):63-72.
Shahidi et al., "Surface Modification Methods for Improving the Dyeability of Textile Fabrics," INTECH Open: Eco-Friendly Textile Dyeing and Finishing, Jan. 16, 2013, 33-52.
SparkFun.com [online], "LilyPad E-Sewing ProtoSnap," available on or before Sep. 21, 2020 via Internet Archive: Wayback Machine URL<https://web.archive.org/web/20200921133248/https://www.sparkfun.com/products/14546>, retrieved on Apr. 25, 2022, retrieved from URL<https://www.sparkfun.com/products/14546>, 7 pages.
Stathakis.com [online], "Perception Is Reality With Regard To The Cleanliness of Your Facility," Jun. 13, 2016, retrieved on Apr. 25, 2022, retrieved from URL<https://www.stathakis.com/blog/perception-is-reality-with-regard-to-the-cleanliness-of-your-facility>, 7 pages.
Sun et al., "Fabric surface properties affected by low temperature plasma treatment," J. Mater. Proc. Technology, Apr. 10, 2006, 173(2):172-177.
Sun et al., "Investigating the Plasma Modification of Natural Fiber Fabrics—The Effect on Fabric Surface and Mechanical Properties," Text. Res. Journal, Sep. 1, 2005, 75(9):639-644.
Textile Fibers, Dyes, Finishes, and Processes: A Concise Guide, 1st ed., Needles (ed.), 1987, 249 pages.
Tsaknaki et al., "Expanding on Wabi-Sabi as a design resource in HCI," Presented at Proceedings of the 2016 CHI Conference on Human Factors in Computing Systems, San Jose, Ca, USA, May 7-12, 2016; CHI '16: Proceedings of the 2016 CHI Conference on Human Factors in Computing Systems, May 2016, 5970-5983.
Tscharn et al., "Ambient light as spatial attention guidance in indoor environments," Presented at Proceedings of The 2016 ACM International Joint Conference on Pervasive and Ubiquitous Computing, Heidelberg, Germany, Sep. 12-16, 2016; UbiComp '16: Proceedings of the 2016 ACM International Joint Conference on Pervasive and Ubiquitous Computing: Adjunct, Sep. 2016, 1627-1630.
Tung et al., "Self-cleaning fibers via nanotechnology: a virtual reality," J. Mater. Chemistry, Apr. 5, 2011, 21:7858-7869.
USANanocoat.com [online], "USA Nanocoat," available on or before Aug. 6, 2020 via Internet Archive: Wayback Machine URL<https://web.archive.org/web/20200806151257/https://www.usananocoat.com/>, retrieved on Apr. 26, 2022, retrieved from URL<https://usananocoat.com/>, 11 pages.
Valero et al., "Recovering spectral data from natural scenes with an RGB digital camera and colored filters," Color Res. Application, Oct. 2007, 32(5):352-360.
Vallgårda et al., "Computational composites," Presented at Proceedings of the SIGCHI Conference on Human Factors in Computing

(56) References Cited

OTHER PUBLICATIONS

Systems, San Jose, Ca, USA, Apr. 28 - May 3, 2007; CHI '07: Proceedings of the SIGCHI Conference on Human Factors in Computing Systems, Apr. 2007, 513-522.

Vogl et al., "StretchEBand: Enabling Fabric-based Interactions through Rapid Fabrication of Textile Stretch Sensors," Presented at Proceedings of the 2017 CHI Conference on Human Factors in Computing Systems, Denver, Co, USA, May 6-11, 2017; CHI '17: Proceedings of the 2017 CHI Conference on Human Factors in Computing Systems, May 2017, 2617-2627.

Wakita et al., "Mosaic textile: wearable ambient display with non-emissive color-changing modules," Presented at Proceedings of the 2006 ACM SIGCHI International Conference on Advances in Computer Entertainment Technology, Hollywood, CA, USA, Jun. 14-16, 2006; ACE '06: Proceedings of the 2006 ACM SIGCHI International Conference on Advances in Computer Entertainment Technology, Jun. 2006, 7 pages.

Wang et al., "A review on the application of photocatalytic materials on textiles," Textile Res. Journal, Nov. 27, 2014, 85(10):1104-1118.

Weng et al., "Preparation of TiO2 thin films on glass surfaces with self-cleaning characteristics for solar concentrators," Surf. Coat. Technology, Sep. 25, 2013, 231:201-204.

Wiberg, "Usability and fun: An overview of relevant research in the hci community," Presented at Proceedings of CHI 2005: Workshop on Innovative Approaches to Evaluating Affective Interfaces, Portland, Or, USA, Apr. 2-7, 2005, 6 pages.

WorkDesign.com [online], "A New Decade Introduces New Lighting Solutions For Human Comfort," Dec. 18, 2019, retrieved on Apr. 25, 2022, retrieved from URL<https://www.workdesign.com/2019/12/a-new-decade-introduces-new-lighting-solutions-for-human-comfort/>, 8 pages.

Xenex.com [online], "LightStrike: Pulsed Xenon Disinfection," available on or before Sep. 20, 2020 via Internet Archive: Wayback Machine URL<https://web.archive.org/web/20200920231034/https://xenex.com/light-strike/>, retrieved on Apr. 25, 2022, retrieved from URL<https://xenex.com/light-strike/>, 5 pages.

Xu et al., "Surface modification of polyester fabric by corona discharge irradiation," Eur. Polym. Journal, Jan. 2003, 39(1): 199-202.

Yao et al., "bioLogic: Natto Cells as Nanoactuators for Shape Changing Interfaces," Presented at Proceedings of the 33rd Annual ACM Conference on Human Factors in Computing Systems, Seoul, Republic of Korea, Apr. 18-23, 2015; CHI '15: Proceedings of the 33rd Annual ACM Conference on Human Factors in Computing Systems, Apr. 2015, 10 pages.

Yu et al., "Indoor air purification using heterogeneous photocatalytic oxidation. Part I: Experimental study," Appl. Catal. B: Environmental, Nov. 9, 2009, 92(3-4):454-461.

Zhang et al., "New understanding of the difference of photocatalytic activity among anatase, rutile and brookite TiO2," Phys. Chem. Chem. Physics, Aug. 5, 2014, 16(38):20382.

Zhang et al., "Study on the photocatalytic and antibacterial properties of TiO2 nanoparticles-coated cotton fabrics," Materials, Jun. 23, 2019, 12(12):2010, 10 pages.

\* cited by examiner

SELF-CLEANING DEVICE

CROSS-REFERENCE TO RELATED APPLICATIONS

This application claims the benefit of U.S. Patent Application No. 63/032,979, filed Jun. 1, 2020, which is incorporated herein by reference.

FIELD

This specification generally relates to self-cleaning devices.

BACKGROUND

Many surfaces are contacted by multiple people throughout the day. These surfaces are typically cleaned manually on a periodic basis. However, such periodic cleaning may not be sufficient to prevent the spread of organic contaminants and germs prior to the next person contacting the surface.

SUMMARY

This specification generally describes self-cleaning devices, such as self-cleaning textile devices. The surfaces can include a photocatalyst that is activated by a light source and that, when activated, cleans and/or decontaminates the surface. The light source can be embedded in the fabric of the device. In some implementations, the self-cleaning device includes one or more threads of light emitting diodes (LEDs) embedded in the fabric of the device and the fabric is coated with a photocatalyst, such as a type or form of titanium dioxide. Other light sources that are embeddable in or behind fabric can also be used in the threads. When the light source is on, the light emitted by the light source activates the photocatalyst causing the photocatalyst to clean and/or decontaminate the surface of the device. This cleaning cycle can be initiated by various triggering mechanisms.

According to some implementations, a self-cleaning device includes a fabric having a surface covered with a photocatalyst, one or more light sources embedded in the fabric, and a triggering mechanism that activates a cleaning cycle by activating the one or more light sources.

Implementations may include one or more of the following features. The one or more light sources can include one or more fabric threads including light sources embedded therein. The one or more fabric threads can be arranged in a pattern such that the one or more light sources emit light onto all areas of the surface when the one or more light sources are active. The one or more light sources can be arranged behind or under the fabric. The device can include a light-diffusing layer arranged between the fabric and the one or more light sources. Each light source can include an LED that emits ultraviolet (UV) light or an LED that emits visible light. The self-cleaning device can include a hydrophobic coating that coats the surface of the fabric. The self-cleaning device can include a light source arranged externally to the fabric surface and configured to activate the cleaning cycle.

The photocatalyst can include titanium dioxide. The photocatalyst can include titanium dioxide doped with one or more elements, the one or more elements including one or more of: lithium, sodium, magnesium, iron, cobalt, gold, vanadium, chromium, manganese, carbon, boron, iodine, fluorine, sulfur, nitrogen or rare earth elements. The surface can be a surface of a seat, an arm rest, clothing, furniture, or the interior surface of a car (e.g., interior car door) or other vehicle.

The triggering mechanism can be configured to activate the one or more light sources based on a schedule or timer. The triggering mechanism can include a pressure sensor. The triggering mechanism can be configured to activate the cleaning cycle in response to detecting a decrease in pressure being applied to the pressure sensor. The pressure sensor can be disposed under or behind the surface. The triggering mechanism can include a light sensor. The triggering mechanism can be configured to activate the cleaning cycle in response to detecting at least a threshold intensity of light.

According to another implementation, a method for manufacturing a self-cleaning device includes obtaining a fabric, coating a surface of the fabric with a photocatalyst, and embedding one or more light sources in the fabric. Embedding the one or more light sources in the fabric can include embedding one or more fabric threads including LEDs into the fabric. Coating a surface of the fabric with a photocatalyst can include pre-treating the fabric using plasma treatment techniques, corona treatment techniques, or flame treatment techniques. The method can include coating the fabric with a hydrophobic coating.

According to another implementation, a self-cleaning seat includes a back portion that includes a fabric surface, a seat portion that includes a fabric surface, and a triggering mechanism. The fabric surface of one or more of the back portion or the seat portion includes a photocatalytic coating and one or more light sources embedded in the fabric. The triggering mechanism is configured to activate a cleaning cycle by activating the one or more light sources.

The one or more light sources can be arranged behind or under the fabric. Each light source can include one of a light emitting diode (LED) that emits ultraviolet (UV) light or an LED that emits visible light. The self-cleaning seat can include a light source arranged externally to the fabric surface and configured to activate the cleaning cycle.

The photocatalyst can include titanium dioxide. The photocatalyst can include titanium dioxide doped with one or more elements, the one or more elements including one or more of: lithium, sodium, magnesium, iron, cobalt, gold, vanadium, chromium, manganese, carbon, boron, iodine, fluorine, sulfur, nitrogen or rare earth elements.

The back portion can include a plurality of back regions. Two or more back regions can each include one or more light sources embedded in the fabric. The triggering mechanism can be configured to selectively activate a cleaning cycle by activating the one or more light sources of the back region. The seat portion can include a plurality of seat regions. Two or more seat regions can each include one or more light sources embedded in the fabric. The triggering mechanism can be configured to selectively activate a cleaning cycle by activating the one or more light sources of the seat region.

The fabric surface of one or more of the back portion or the seat portion that includes the photocatalytic coating and the one or more light sources embedded in the fabric can further include a hydrophobic coating that coats the surface of the fabric.

The methods in accordance with the present disclosure can include any combination of the aspects and features described herein. That is, methods in accordance with the present disclosure are not limited to the combinations of aspects and features specifically described herein, but also may include any combination of the aspects and features provided.

The subject matter described in this specification can be implemented in particular embodiments so as to realize one or more of the following advantages.

In accordance with an aspect of the present disclosure, a fabric surface of a self-cleaning device is covered with a photocatalyst. When the photocatalyst is activated by light, reactive substances, e.g., hydroxyl radicals and superoxide radical anions, are formed. These reactive substances decompose organic compounds (e.g., to clean stains), eliminates bad smells, and kills organic contaminants, germs, and/or bacteria. Titanium dioxide in different types and forms has shown great potential as a powerful photocatalyst for various significant reactions due to its chemical stability, nontoxicity, and high reactivity. By leveraging these and other textile coatings, such as hydrophobic or polytetrafluoroethylene nanoparticles coatings, textiles can be created that are easy to clean infrequently, that can repel liquids and bodily fluids, and that can self-clean during the day reducing the potential for viruses and bacteria to build up on surfaces in public spaces and infect individuals.

Implementations of self-cleaning devices can include a triggering mechanism that initiates a cleaning cycle at appropriate times, e.g., when a person gets up from a self-cleaning seat. In this way, a self-cleaning seat can be cleaned after each use and prior to the next person sitting in the seat, making the seat more sanitary. For instance, energy may be conserved by only cleaning the surfaces when needed. As the seats are cleaned more frequently, the cleaning cycles can be shorter, further reducing energy consumption.

Implementations of the present disclosure can include one or more optional features that can improve the efficacy of the self-cleaning cycles. For instance, some types of fabric (e.g., fabric made of polyester fibers) may have chemically inert and nonporous surfaces with low surface tensions that make it difficult to adhere a coating. Pre-treating the fabric prior to coating may improve the adhesion of the coating to some types of fabric. Pre-treating the fabric can include washing the fabric to remove surface contaminants on the fabric. In some instances, a primer can improve the adhesion between the fabric and the coating. In instances in which a pre-treatment process has been performed, the coating may be applied as soon as possible after the pre-treatment process to improve coating retention and prevent a potential drop in pre-treatment efficacy.

Implementations of the self-cleaning devices can include additional elements that help to focus light from one or more light sources onto the fabric. Such elements can include reflectors built into the one or more light sources or reflective or refractive layers arranged adjacent to the one or more light sources to name some examples.

The details of one or more implementations of the present disclosure are set forth in the accompanying drawings and the description below. Other features and advantages of the present disclosure will be apparent from the description and drawings, and from the claims.

DETAILED DESCRIPTION

This document generally describes self-cleaning devices and methods for manufacturing self-cleaning devices. The self-cleaning devices can be in the form of (or a part of) various types of seats, arm rests, furniture, clothing, carpet, towels, oven mitts, pet beds, or other objects that can be made of fabric. For example, self-cleaning seats can be used in movie theaters, ride-share cars, airplanes, trains, boats, restaurants, or other vehicles or areas that multiple people come into contact with the seats.

Figure 1:
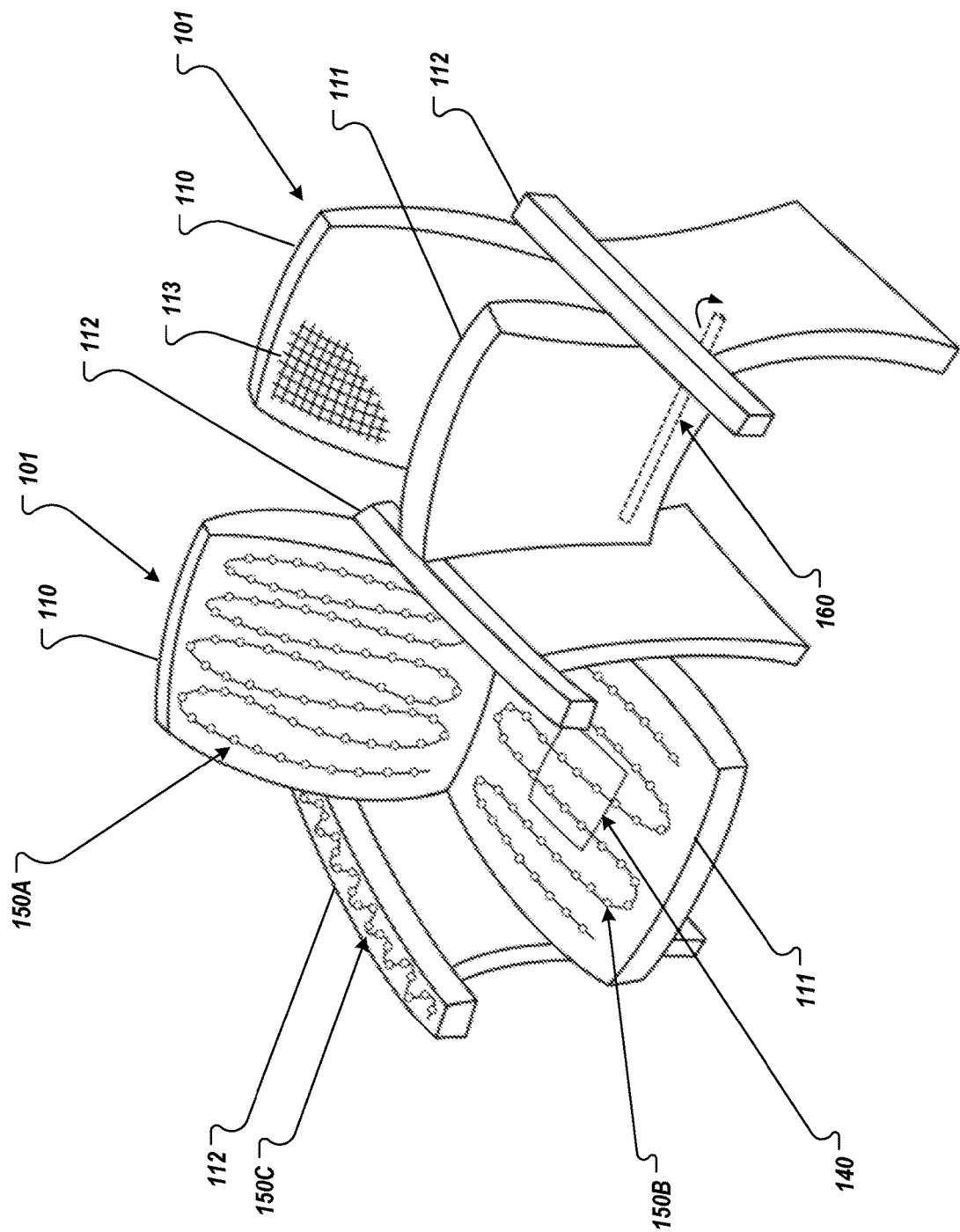
FIG. 1 depicts an example self-cleaning device.

FIG. 1 depicts example self-cleaning devices 101. In this example, the self-cleaning devices are in the form of self-cleaning seats. The self-cleaning seats 101 include a back portion 110 having an outer surface 113 made at least partially of a fabric, a seat portion 111 having an outer surface made at least partially of a fabric, and arm rests 112 having an outer surface made at least partially of a fabric. For the purpose of this document, a fabric is a material made of textile fibers, e.g., by weaving or knitting the fibers. The seat portion 111 can be mounted to pivot about a rod 160. The seat 101 may include a resilient spring (not shown) that biases the seat 101 in the closed position shown on the right of FIG. 1. The seat portion 111 can be moved downward to the open position shown on the left of FIG. 1. When the seat portion 111 is released, e.g., when a person gets out of the self-cleaning seat 101, the resilient spring may return the seat portion 111 the closed position. The seats 101 may be part of a row of identical seats. In some instances, the seats 101 of FIG. 1 may be different, e.g., with respect to the fabric construction or the triggering mechanisms described below.

The fabric surface of each portion 110-112 of the self-cleaning seat 101 can be coated with a photocatalyst, such as a type or form of titanium dioxide ($TiO_2$). When the photocatalyst is activated by light, reactive substances, e.g., hydroxyl radicals and superoxide radical anions, are formed. These reactive substances decompose organic compounds (e.g., to clean stains), eliminate bad smells, and kill organic contaminants, germs, and/or bacteria.

Visible light-responsive photocatalysts can be created by adding small amounts of cations and metal oxides by both chemical doping and physical ion-implantation methods to normally purely UV-active $TiO_2$. Other modification methods include impurity doping (chemical and physical), semiconductor coupling, dye sensitization, etc.

The following materials have been researched as being effective in enhancing $TiO_2$'s photocatalytic properties with visible light: doping of $TiO_2$ nanoparticles with Li, Na, Mg, Fe and Co nitrates; deposition of Au onto $TiO_2$; doping of $TiO_2$ with transition metals such as Cr, Fe and V; doping with rare earth elements; and doping of $TiO_2$ with non-metal dopants such as C, B, I, F, S and N.

For self-cleaning purposes, some (non-exhaustive) modifications to $TiO_2$ include $TiO_2/SiO_2$/graphene oxide nanocomposites; porphyrin dye/$TiO_2$ coating used for PET fibers; N—$TiO_2$ film and loading AgI in cotton fibers; manganese doped $TiO_2$ nanoparticles; $TiO_2$ films modified with Au nanoclusters; $TiO_2$-$Al_2O_3$ coatings; and $TiO_2$/Pt/$WO_3$ hybrid films.

There are various ways to activate the photocatalyst of the self-cleaning seats 101. In one example, a light source (not shown in FIG. 1) disposed in the same room or area as the self-cleaning seats 101 can emit light onto the photocatalysts. For example, lights in the ceiling of a theater can activate photocatalyst of theater seats when the seats 101 are not in use, e.g., between movies.

FIG. 1 schematically shows an internal view of some of the fabric surfaces of the seats 101. The depicted elements may not be visible from the outside, as indicated by the seat 101 on the right that is in the closed position. In addition to light from outside light sources, each seat 101 can include one or more onboard light sources to activate the photocatalyst that covers the fabric surfaces. For example, the self-cleaning seat 101 includes a first thread of light sources 150A for the back portion 110, a second thread of light sources 150B for the seat portion 111, and a third thread of light sources 150C for each arm rest 112. Each thread of light sources 150A-150C includes a set of lights that can be turned on to activate the photocatalyst during cleaning cycles and turned off to end the cleaning cycles.

The lights in the threads of light sources 150A-150C and the other light sources described in this disclosure can include LEDs. The LEDs can be visible light LEDs that emit visible light, ultraviolet (UV) lights that emit UV light, depending on the photocatalyst material. Traditional photocatalysts respond to ultraviolet light that can be produced in a variety of wavelengths (e.g., 100-400 nanometers (nm)) but these can cause damage to human tissues such as eyes and skin. Instead of using potentially harmful wideband UV light, a specific wavelength (e.g. 222 nm) of far-UVC may be chosen instead. The $TiO_2$ coating can be modified by doping with abovementioned elements to have antibacterial and cleaning effects when activated by visible light (400-700 nm) alone, as described above.

The light sources can be very small LEDs that are embedded in fibers that make the fabrics light up at scale. That is, each thread of light sources 150A-150C can include a thread of fibers with LEDs embedded therein. Such light sources can include LED strands, LED fibers, fiber optics, or electroluminescent wires. The threads of light sources 150A-150C can be interwoven into the fabric of the back portion 110, the seat portion 111, and each arm rest 112, respectively. In another example, the threads of light sources 150A-150C can be disposed under or behind the fabric surfaces. Although FIG. 1 depicts threads of light sources 150A-150C, implementations of the self-cleaning seats 101 can also include the light sources described, e.g., in reference to FIGS. 5 and 6A to 6F.

The light sources can be arranged such that the light emitted by the light sources diffuse and hit every part of their respective fabric surface. This arrangement can include an appropriate spacing between adjacent light sources and an appropriate spacing between adjacent runs of light sources from one end of the fabric surface to the other end of the fabric surface. The spacing can be based on the size of the light sources, the intensity of the light sources, and/or the type of fabric in which the light sources are embedded.

Figure 2:
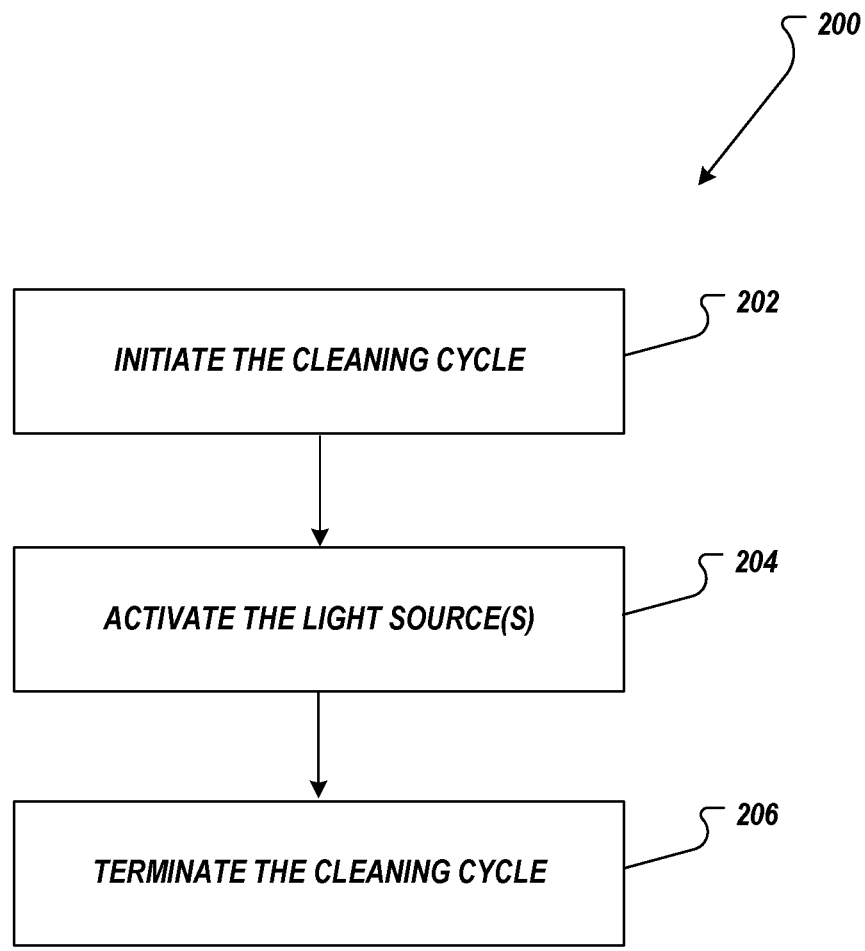
FIG. 2 depicts an overview of a cleaning cycle.

FIG. 2 is a schematic overview of an example cleaning cycle 200. The cleaning cycle 200 can include initiating 202 the cleaning cycle, activating 204 one or more onboard and/or external light sources, and terminating 206 the cleaning cycle. The cleaning cycle 200 is applicable to any of the self-cleaning devices of the present disclosure.

The cleaning cycle can be initiated using a triggering mechanism. In some instances, the seat 101 includes a triggering mechanism 140 that is arranged in the seat portion 111. For example, the triggering mechanism 140 can include a pressure sensor installed in the seat portion 111. The pressure sensor can include a pressure-sensitive sheet, e.g., Velostat™, force sensitive resistors, or another appropriate type of pressure sensor. The pressure sensor can also include conductive thread or fabrics that make contact with one another when pressure is applied. The triggering mechanism can also include a controller, e.g., a microcontroller or other control circuitry, connected to the threads of light sources 150A-150C and the pressure sensor. The pressure sensor can provide, to the controller, an indication of the amount of pressure being applied to the seat portion, e.g., in the form of a change in current or voltage. Based on this indication, the controller can determine when a person is sitting in the self-cleaning seat 101 or when a person has left the self-cleaning seat 101. The controller can be configured to initiate a cleaning cycle when a person gets out of the self-cleaning seat 101, e.g., to clean the self-cleaning seat 101 between each occupancy of the self-cleaning seat 101.

In FIG. 1, the triggering mechanism 140 is shown as a flat sheet, e.g., that includes a pressure-sensitive sheet, that covers a central region of the seat portion 111. In other examples, a triggering mechanism 140 that is arranged in or below the fabric surface may cover a larger or smaller portion of the fabric surface.

The self-cleaning seat 101 can also include a mechanical triggering mechanism that initiates a cleaning cycle in response to the seat portion 111 of the self-cleaning seat 101 moving into the closed or up position when a person gets out of the self-cleaning seat 101. When seat portion 111 pivots about the rod 160, it can press or release an end stop limit switch, a potentiometer, an encoder, a Hall effect sensor, or a mechanical button or switch, triggering the cleaning cycle. Similarly to the pressure sensor, a mechanical triggering mechanism can include a controller, e.g., a microcontroller, connected to the threads of light sources 150A-150C and the aforementioned component.

Other triggering mechanisms can also be used. For example, the threads of light sources 150A-150C can also include light sensors that are also connected to a controller. When light is detected by the light sensors, indicating that a person is not sitting in the self-cleaning seat 101, the controller can initiate the cleaning cycle. In another example, a controller (e.g., server) in the cloud can control the cleaning cycles of multiple self-cleaning seats, e.g., based on a timer.

In another example, a motion or occupancy sensor can be used to initiate the cleaning cycles of self-cleaning seats 101. For example, when a theater room transitions from an occupied state to a non-occupied state, the cleaning cycle for each self-cleaning seat 101 in the room can be initiated.

In another example, the triggering mechanism 140 can include a moisture sensor. In this example, the triggering mechanism can initiate a cleaning cycle in response to detecting moisture on a surface, e.g., on a seat, as this can be indicative of a spilled liquid. Prior to initiating the cleaning cycle, the triggering mechanism can detect whether a person is sitting in the seat, e.g., using the pressure sensor or occupancy sensor described above. If a person is not detected, the triggering mechanism can initiate the cleaning cycle. In another example, a pH sensor can be used to check the pH of any detected moisture. If a liquid that contacts the surface has a pH within a particular range, the triggering mechanism can initiate a cleaning cycle.

In another example, the cleaning cycle can be initiated automatically or manually after an event. A controller can use ticket purchasing information to determine which seats were occupied and initiate cleaning cycles for the seats that were occupied, while not initiating cleaning cycles for unoccupied seats. This can be used in combination with mechanical triggering mechanisms and/or occupancy sensors to determine whether non-purchased seats were nonetheless occupied at some point during the event.

Referring again to FIGS. 1 and 2, a cleaning cycle for the self-cleaning seat 101 can include activating, i.e., turning on the threads of light sources 150A-150C. When the light sources are on, the light emitted by the light sources activate the photocatalyst, causing a reaction that creates reactive substances that decompose organic compounds on the fabric surfaces of the back portion 110, the seat portion 111, and the arm rests 112. The threads of light sources 150A-150C can be controlled independently in some cases. For example, the light sources 150A can be activated while the light sources 150B and 150C are not activated.

A self-cleaning device can have multiple regions that are cleaned differently and/or separately. For example, some regions may be more prone to stains or contaminants than other regions. In this example, the regions that are more prone to stains or contaminants can be cleaned for longer periods of time and/or with higher intensity light. Each region can have separate light sources that are activated for a cleaning cycle for the region.

Figure 3:
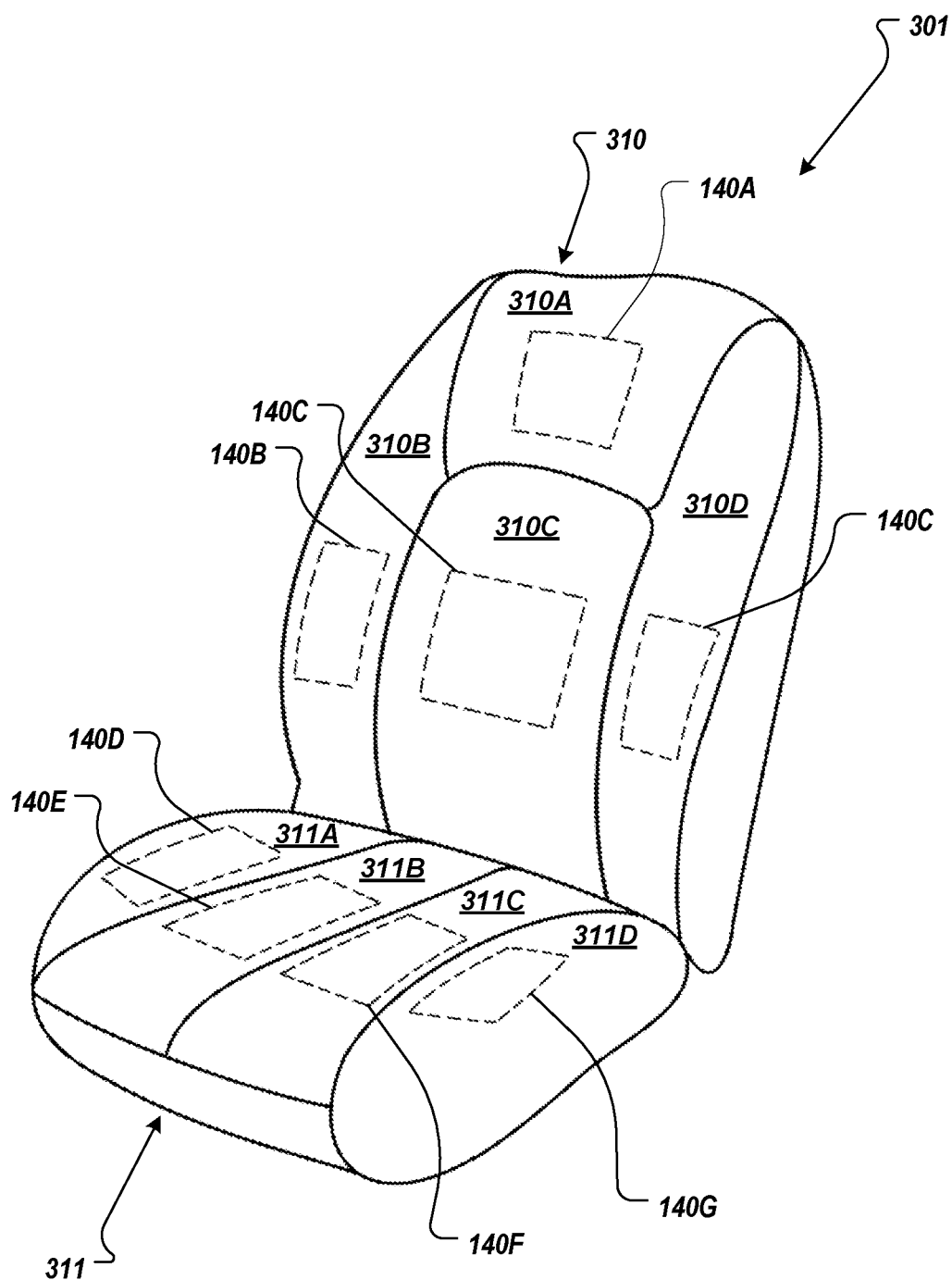
FIGS. 3 and 4 each depict further examples of self-cleaning devices.

For instance, FIG. 3 depicts an example of a further self-cleaning seat 301. The self-cleaning seat 301 includes a back portion 310 and a seat portion 311 that each include an outer surface made of fabric. The back portion 310 includes multiple back regions 310A-310D that are separated, e.g., by seams. Similarly, the seat portion 311 includes multiple seat regions 311A-311D that are separated by seams. As illustrated, each region 310A-310D and 311A-311D can include a triggering mechanism 140A-140G that is specific to that region. The triggering mechanisms 140A-140G can be configured to selectively activate the light source(s) for particular regions. Selectively activate can mean that the light source(s) for some regions 310A-310D are activated and not for other regions 310A-310D. Selectively activate can also mean that the light source(s) are activated for different durations and/or that light intensity differ across regions. Although not shown in FIG. 3, each region 310A-310D and 311A-311D includes one or more light sources embedded in the fabric.

Figure 4:
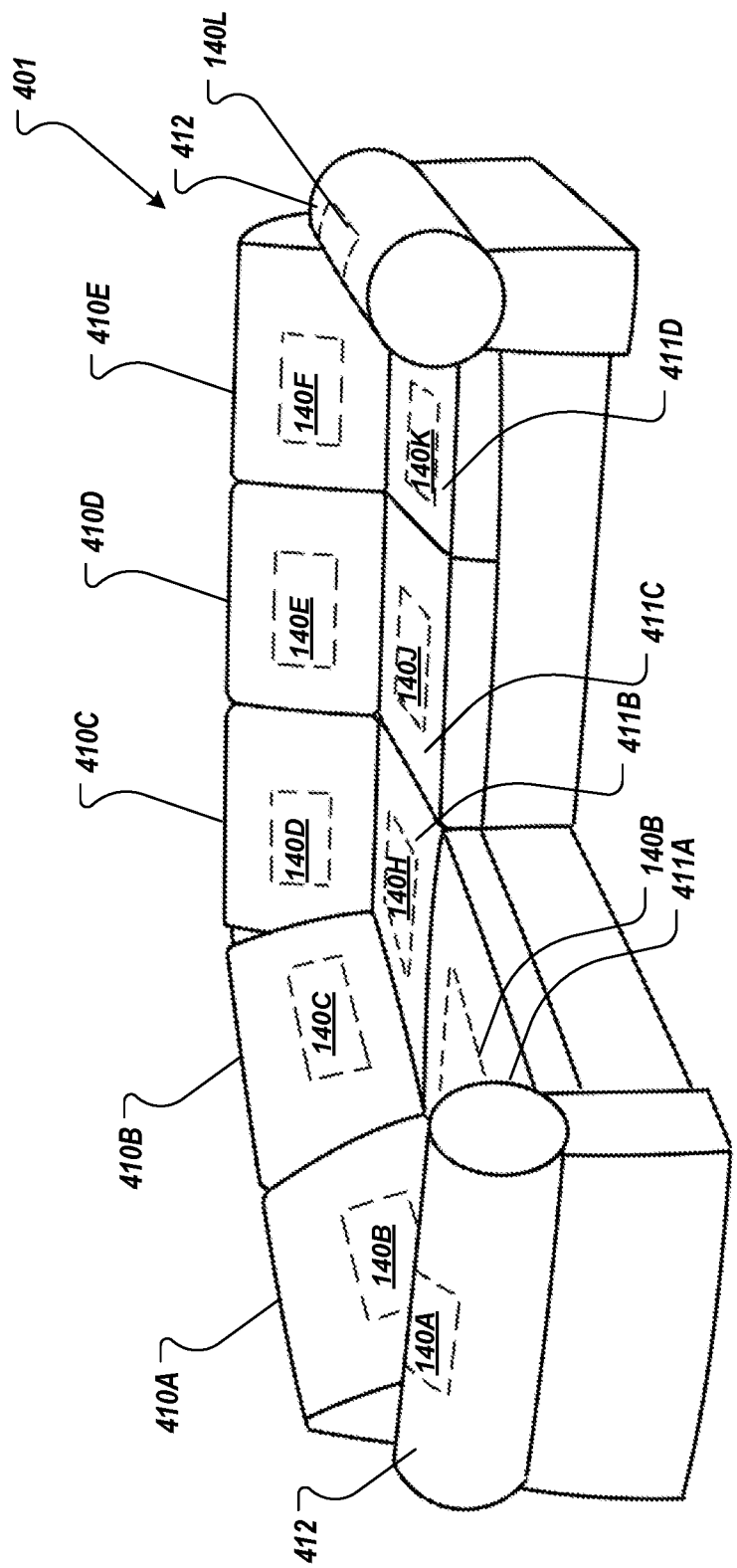

FIG. 4 depicts a further example of a self-cleaning seat 401. In FIG. 4, the self-cleaning seat 401 is a large sectional sofa that may seat multiple people at once. The seat 401 includes multiple back portions 410A-410E, a plurality of seat portions 411A-411D, and a pair of arm rests 412. The back portions 410A-410E, the seat portions 411A-411D, and arm rests 412 each include an outer surface made of fabric. Similarly to FIG. 3, the seat 401 includes multiple triggering mechanisms 140A-140K that allow selective activation of the cleaning cycles. Although not shown in FIG. 4, each portion 410A-410E and 411A-411D includes one or more light sources embedded in the fabric.

Referring again to FIG. 2, the example cleaning cycle 200 includes terminating 206 the cleaning cycle 200 by deactivating, i.e., turning off, the one or more light sources. In some instances, the light sources are deactivated in response to a timer for the cleaning cycle expiring. In instances in which the cleaning cycle 200 is initiated manually, the cleaning cycle 200 can also be terminated manually.

Figure 5:
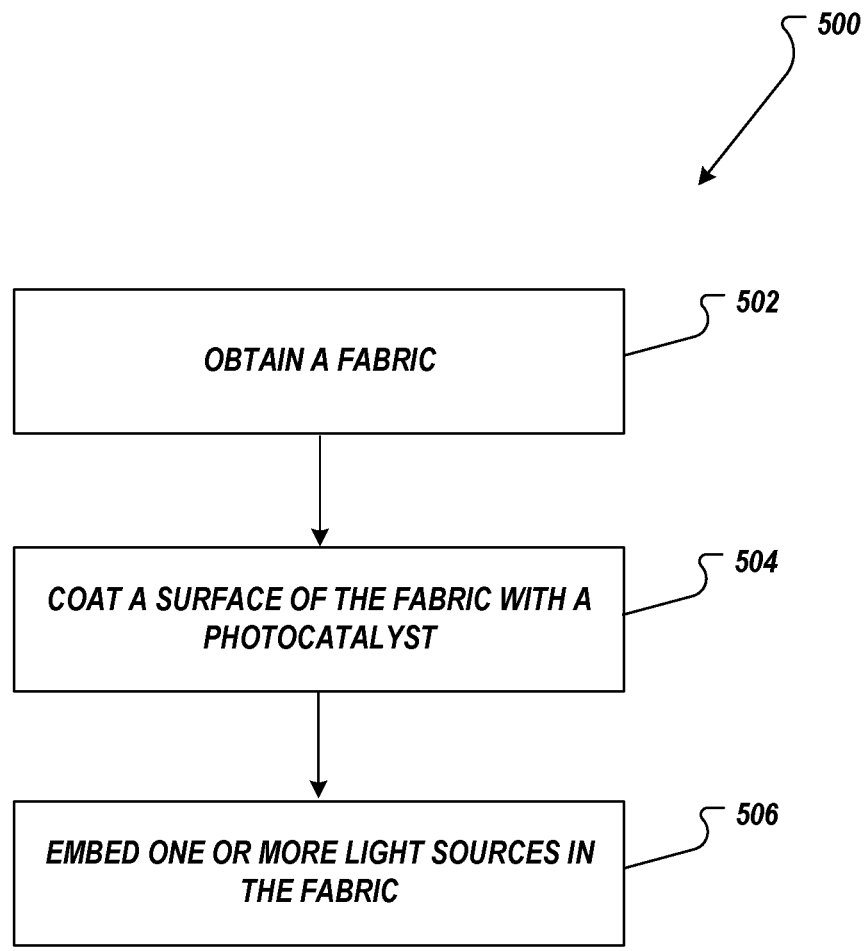
FIG. 5 depicts an overview of a method according to the present disclosure.

FIG. 5 is a schematic overview of a method 500 of manufacturing a self-cleaning device. For example, the method 500 can be used to manufacture the fabric outer surface of any of the self-cleaning seats 101, 301, 401 described above. The method 500 includes obtaining 502 a fabric that will be disposed on the surface of the device, coating 504 the outer surface of the fabric with a photocatalyst, and embedding 506 one or more light sources in the fabric.

In some instances, coating 504 the outer surface of the fabric with a photocatalyst can include pre-treating the fabric. Pre-treating the fabric can include the use of plasma treatment, corona treatment, or flame treatment to name a few examples. Pre-treating the fabric can also include washing the fabric before the plasma treatment, corona treatment, or flame treatment. The fabric can be washed in a sonicated bath using non-ionic detergent, for example. Optionally, a primer may be applied after the plasma treatment, corona treatment, or flame treatment.

Plasma treatment exposes the fabric surface to plasma gas. The plasma gas particles can modify the properties of the fabric fibers by depositing chemical materials (referred to as "plasma polymerization") or by removing material (referred to as "plasma etching"). The plasma gas is an ionized gas with equal density of positive and negative charges that exist across a wide temperature and pressure range. Depending on the specific gas, plasma gas can include free electrons, ions, and free radicals, for example. Unlike submersion-based pre-treatment processes, the plasma gas particles modify the surface structure of the fibers that allow coating to adhere to the fibers without modifying the fibers' internal structure.

Corona treatment exposes the fabric surface to high-frequency corona discharge (electrically ionized air) that increases the functional groups on the fabric surface that allow the photocatalytic coating to adhere to the fabric. Specifically, corona treatment increases the surface tension of the fabric fibers. Specifically, corona discharge breaks oxygen molecules at the atomic level. The resulting atoms bond with molecule ends of the fabric fibers, resulting in a chemically active surface that is receptive to adhesives, inks, and coatings.

Flame treatment exposes the fabric surface to ionized hydrocarbon gas. Flame treatment can create oxidized species on the fiber surface, as well as form hydroxyl, carboxyl and carbonyl functionalities. In some instances, flame treatment can achieve high surface energy levels (dyne levels) at high production speeds.

In addition to or separately from a pre-treatment process, coating 504 the outer surface of the fabric with a photocatalyst can utilize spraying, painting, direct coating or floating knife coating, direct roll coating, or padding techniques to name a few examples. In instances in which a pre-treatment process has been performed, the coating may be applied as soon as possible after the pre-treatment process.

Direct coating or knife coating applies a viscous photocatalyst to the fabric while the fabric is placed under tension and run below a knife blade. The distance between the fabric surface and the knife blade can be adjusted to adjust the thickness of the coating. The angle between then fabric surface and the knife blade can also be adjusted to modify coverage of the coating on the fabric. Direct coating may be suited for filament yarns.

Direct roll coating uses a roller suspended in a liquid photocatalyst solution to roll the solution across the fabric surface. Excess solution may be scraped from the roller using a blade arranged adjacent to the roller.

Padding can include submerging the fabric in a liquid photocatalyst solution and using rollers to remove the excess solution.

In the present examples, coating 504 the outer surface of the fabric with a photocatalyst can further include drying, and optionally curing, the coated fabric.

In some instances, the method 500 further includes coating the fabric with a hydrophobic coating before or after the fabric has been coated with the photocatalyst.

Referring in addition to FIGS. 6A to 6H, examples of self-cleaning devices 600 that can be obtained using the method 500 are explained. The self-cleaning devices 600 can be incorporated, e.g., into the self-cleaning seats 101, 301, 401 in FIGS. 1, 3, and 4.

Figure 6A:
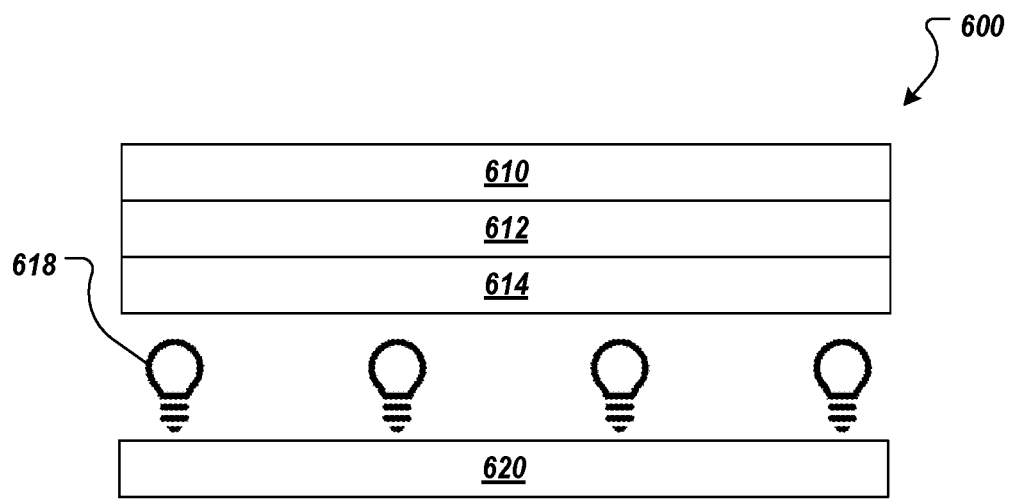
FIGS. 6A to 6H depict further examples of self-cleaning devices.
Figure 6B:
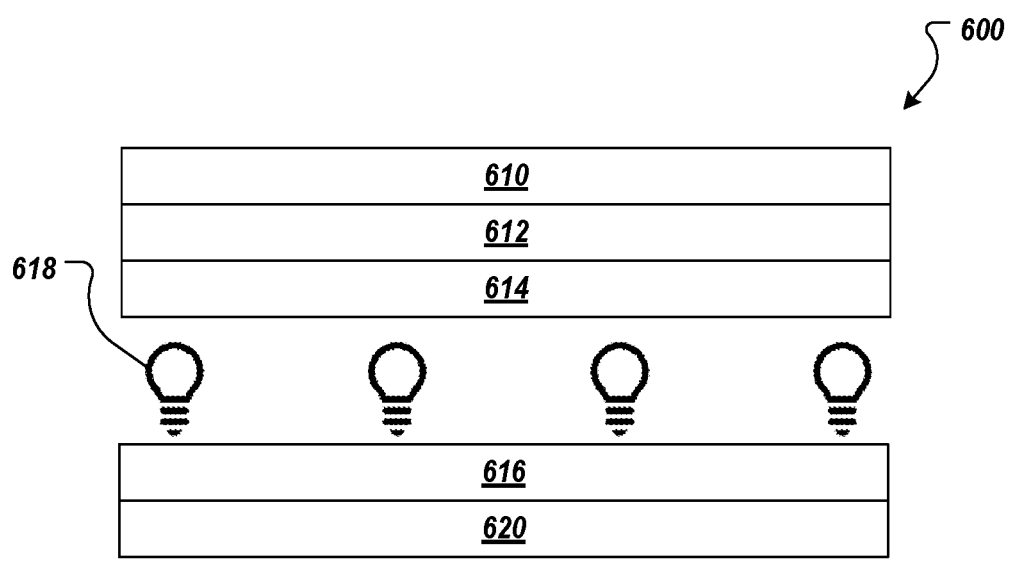
Figure 6C:
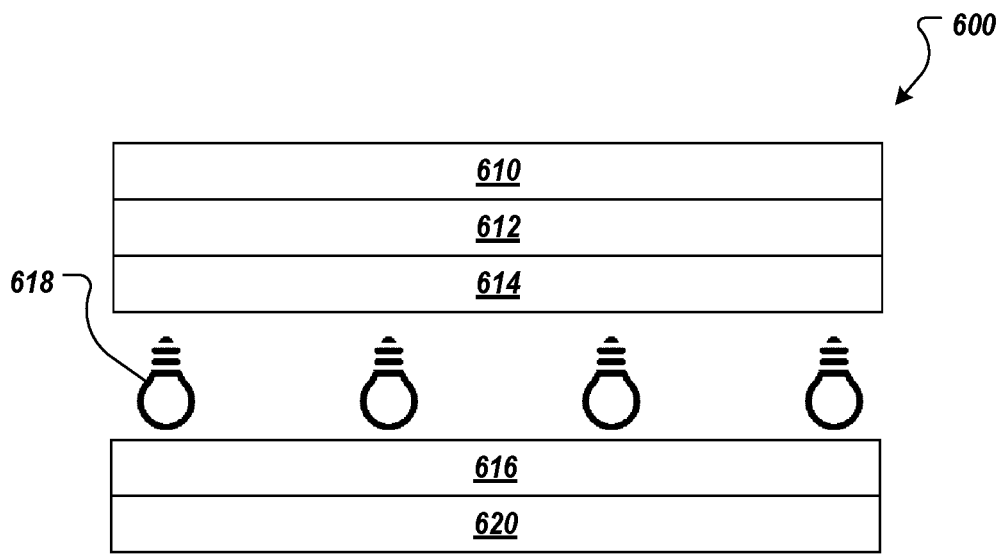
Figure 6D:
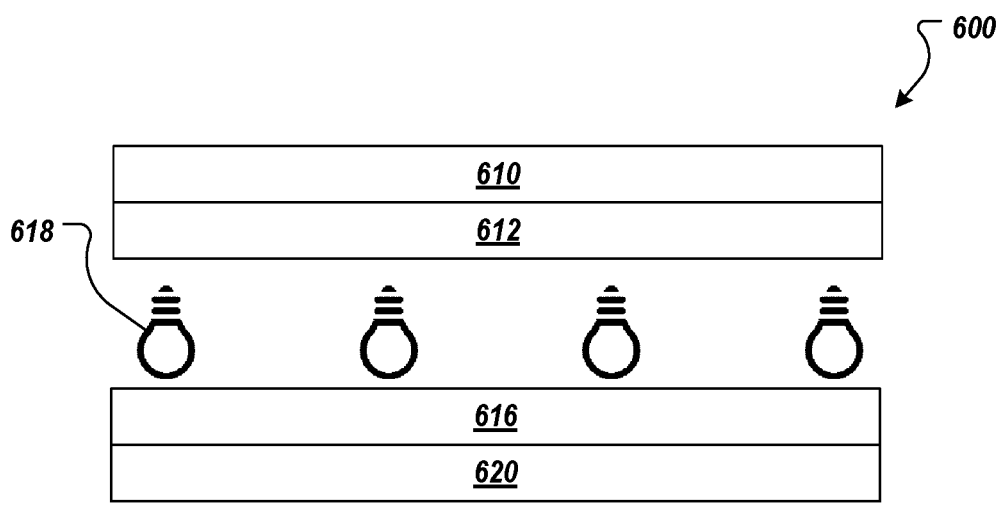
Figure 6E:
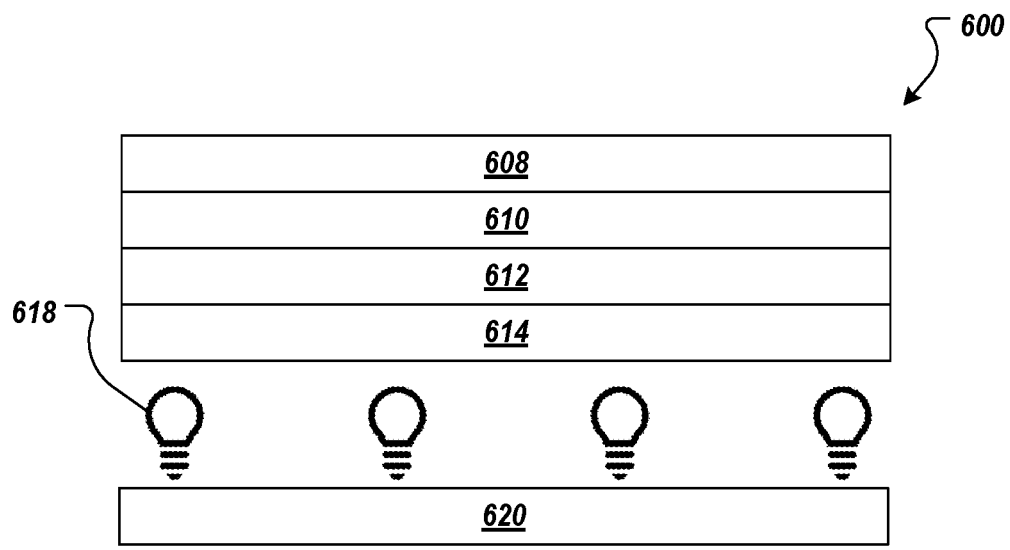
Figure 6F:
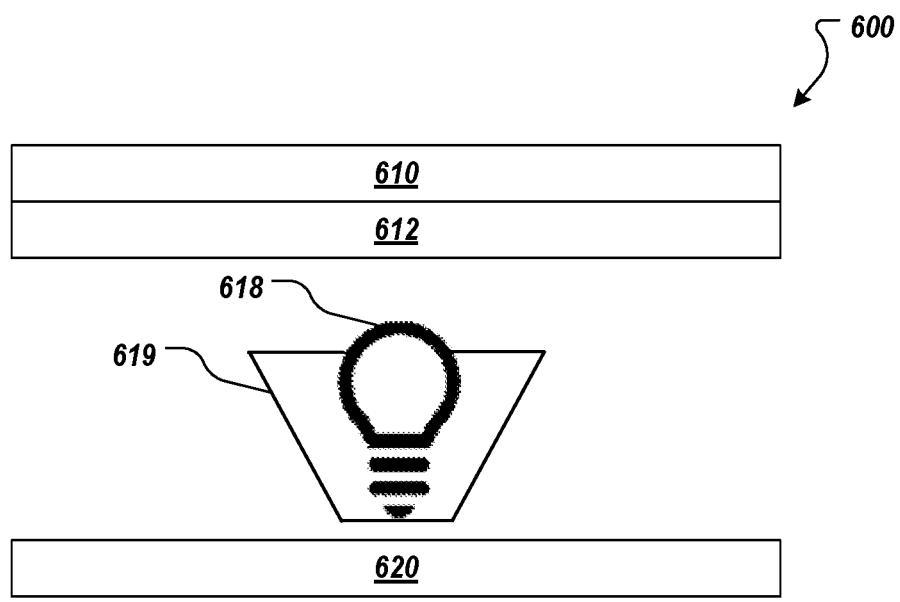
Figure 6G:
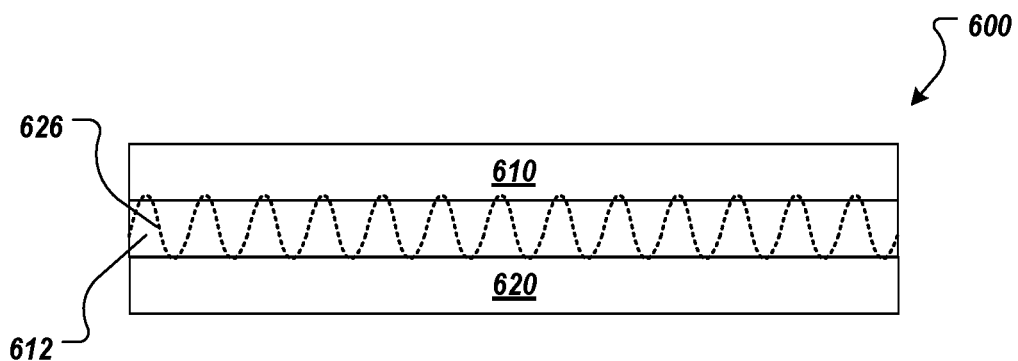
Figure 6H:
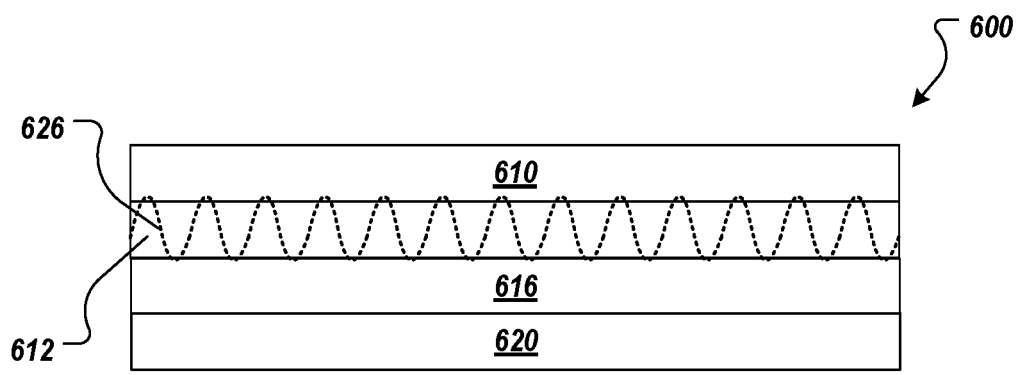

As described, the method 500 includes obtaining 500 a fabric 612, as shown in each of FIGS. 6A to 6H. In some instances, the fabric 612 is a material made of natural or synthetic fibers, e.g., by weaving or knitting the fibers. As shown in FIGS. 6G and 6H, the fabric 612 may be a fiber optic fabric that includes ultra-thin optical fibers such as the threads 626 woven or stitched into a synthetic fabric 612.

The method 500 further includes coating 504 the outer surface of the fabric 612 with a photocatalyst using any of the techniques described above, for example. Thus, the self-cleaning devices 600 each include a photocatalytic coating 610 arranged on top of the fabric. Although FIG. 6A to 6H schematically depict the photocatalytic coating 610 as a distinct layer arranged above the fabric 612, the photocatalytic coating may penetrate into the fabric 612 and coat the individual fabric fibers.

In some cases, the method 500 further includes coating the photocatalytic coating 610 with a hydrophobic coating 608 (FIG. 6E). The hydrophobic coating 608 or superhydrophobic coating may be configured to repel water or other liquids. For example, if a liquid is spilled onto the self-cleaning device 600, the hydrophobic coating 608 may cause the liquid to form beads that roll off the surface of the device 600. Any residual contaminants that penetrate the fabric 612 may be neutralized using the process described in reference to FIG. 2.

Although FIG. 6E depicts the optional hydrophobic coating 608 above the photocatalytic coating 610, the hydrophobic coating 608 may be arranged below the fabric 612 in some implementations. For example, if a liquid is spilled onto the self-cleaning device 600, the photocatalytic coating 610 and the fabric 612 may absorb the spill. The hydrophobic coating 608 may prevent seepage and penetration of the spilled liquid into the other elements of the device 600, e.g., the light diffusing fabric 614 or the light source(s) 618. Meanwhile, the fabric 612 may be cleaned using the process described in reference to FIG. 2.

The method 500 further includes embedding 506 one or more light sources 618 in the fabric. For example, one or more threads 626 of fibers having LEDs embedded therein can be interwoven or intertwined into the fabric (FIGS. 6G and 6H). In other examples, one or more light sources 618 can be disposed behind or under the fabric 612. Thus, in the present disclosure, the expression "embedded" is not limited to embodiments in which the light source is interwoven or intertwined with the fibers of fabric 612.

In some instances, the one or more light sources 618 can include LEDs. The LEDs can be visible light LEDs that emit visible light, ultraviolet (UV) lights that emit UV light, depending on the photocatalyst material. The light sources 618 can include LED strands, LED fibers, fiber optics, or electroluminescent wires. The light sources 618 can include individual LEDs that are attached to an underside of the fabric 612. The light sources 618 can also include printed LEDs. The number of light sources 618 may vary. For example, as shown in FIG. 6F, a single large light source 618 may be arranged to illuminate the fabric 612. Such a light source may emit fluorescent or incandescent light.

The light sources 618 can be arranged in a pattern such that the light sources emit light that diffuses and hits every part of the coated surface. As shown, e.g., in FIGS. 6A, 6B, 6E, and 6F, the one or more light sources 618 can be arranged facing the fabric 612. In other examples, the one or more light sources 618 can be arranged facing away from the fabric 612 (FIGS. 6C and 6D. As shown in FIGS. 6G and 6H, the light source 626 may not have a specific directionality towards or away from the fabric 612. Independently of the direction in which the one or more light sources 618 are facing, the method 500 may further include arranging a reflective or refractive layer 616 below the one or more light sources 618, i.e., on the side of the light source(s) 618 opposite from the fabric 612. For example, the reflective layer 616 may include a flexible film that includes biaxially-oriented polyethylene terephthalate (boPET).

As shown in FIGS. 6A, 6B, 6C, and 6E, the method 500 can further include arranging a light-diffusing fabric 614 between the fabric 612 and the one or more light sources 618. The light-diffusing fabric 614 spreads the light emitted by one or more discrete light sources 618 evenly across the coated fabric 612. For example, the light-diffusing fabric 614 may be a white, translucent fabric made of polyester. However, some examples may not require a light-diffusing fabric 614. For example, the light source 618 may include a light-diffusing panel or a diffused LED backlight with built-in diffusion capabilities. In some instances, the light source may include a diffusing element, such as the reflective layer 616 (FIG. 6D) or a cone 619 (FIG. 6F) that focuses the light from the light source 618 across the fabric layer 612. In other examples, the light sources are distributed throughout the fabric 612, e.g., in the threads 626 shown in FIGS. 6G and 6H.

The method 500 can further include providing a backing 620 to support the self-cleaning device 600. In some instances, the backing 620 can be integral to the one or more light sources 618, e.g., part of a LED light panel. The backing 620 may also be a thin substrate that results in a self-cleaning device 600 with a low height profile that can be mounted on the surface of an existing object (e.g., as a fabric cover). Referring again to FIGS. 1, 3, and 4, the backing 620 of FIGS. 6A to 6H may also schematically represent a larger structure, i.e., the portions of a back portion 110, 310, 410 or seat portion 111, 311, 411 apart from the outer fabric surface. Such a design may enable the integration of a smaller number of larger light sources, as shown in FIG. 6F.

The method 500 can further include connecting the one or more light sources to a controller, as described above, and optionally to a triggering mechanism, such as triggering mechanism 140. Depending on the specific design, the triggering mechanism 140 may be arranged above the backing 620 shown in FIGS. 6A-6H. In some instances, the backing 620 may be thin and flexible enough so that the entire self-cleaning device 600 as shown can be arranged on top of a suitable triggering mechanism 140.

Embodiments of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory program carrier for execution by, or to control the operation of, data processing apparatus. Alternatively or in addition, the program instructions can be encoded on an artificially generated propagated signal, e.g., a machine generated electrical, optical, or electromagnetic signal, that is generated to encode information for transmission to suitable receiver apparatus for execution by a data processing apparatus. The computer storage medium can be a machine readable storage device, a machine readable storage substrate, a random or serial access memory device, or a combination of one or more of them. The computer storage medium is not, however, a propagated signal.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a stand alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program include, by way of example, can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) monitor, an LCD (liquid crystal display) monitor, or an OLED display, for displaying information to the user, as well as input devices for providing input to the computer, e.g., a keyboard, a mouse, or a presence sensitive display or other surface. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending resources to and receiving resources from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client server relationship to each other.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A device, comprising:
   a portion that is constructed for repeated use by different living beings;
   a fabric that covers the portion and that is coated with a photocatalyst, the fabric having a surface that is exposed to contaminants or germs through the repeated use by the different living beings;
   one or more fiber optic light sources that are embedded in the fabric in a pattern that, when activated, allows diffused light to illuminate all of the fabric surface that is exposed to the contaminants or the germs through the repeated use by the different living beings; and
   a triggering mechanism that selectively activates the one or more fiber optic light sources that are embedded in the fabric in the pattern, thereby initiating a self-cleaning cycle of the fabric surface that is exposed to the contaminants or the germs through the repeated use by the different living beings, wherein the triggering mechanism comprises a controller and a light sensor which is included in threads of the one or more fiber optic light sources, and wherein the controller is configured to:
   determine detection of at least a threshold intensity of light by the light sensor;
   determine that the portion is unoccupied based on the detection of the threshold intensity of light; and
   initiate the self-cleaning cycle of the fabric surface based on the determination that the portion is unoccupied.

2. The device of claim 1, wherein the one or more fiber optic light sources comprise a single fiber optic thread that is embedded in a zig-zag pattern in the fabric.

3. The device of claim 1, wherein the one or more fiber optic light sources are arranged behind or under the fabric.

4. The device of claim 1, further comprising a light-diffusing layer arranged between the fabric and the one or more fiber optic light sources.

5. The device of claim 1, wherein each of the one or more fiber optic light sources comprises a light emitting diode (-LED) that emits visible light.

6. The device of claim 1, wherein the photocatalyst comprises titanium dioxide.

7. The device of claim 1, wherein the photocatalyst comprises titanium dioxide doped with one or more elements, the one or more elements comprising one or more of:
   iron, cobalt, chromium, gold, vanadium, manganese, carbon, boron, iodine, fluorine, sulfur, nitrogen or rare earth elements.

8. The device of claim 1, wherein the triggering mechanism is further configured to activate the one or more fiber optic light sources based on a schedule.

9. The device of claim 1, wherein the triggering mechanism further comprises a pressure sensor, and wherein the triggering mechanism is further_configured to activate the one or more fiber optic light sources in response to detecting a decrease in pressure being applied to the pressure sensor.

10. The device of claim 1, wherein the portion comprises a seat back, an armrest, or a seat cushion.

11. The device of claim 1, wherein the triggering mechanism comprises circuitry that includes a force-sensitive resistor.

12. The device of claim 1, wherein the repeated use by the different living beings comprises physical contact by the different living beings.

13. The device of claim 1, wherein the repeated use by the different living beings comprises public use.

14. The device of claim 1, wherein the triggering mechanism selectively activates the one or more fiber optic light sources based on receiving a user input from a particular one of the different living beings indicating that the particular one of the different living beings has finished using the device.

15. The device of claim 1, wherein the triggering mechanism selectively activates the one or more fiber optic light sources after determining that one of the different living beings has just completed using the portion.

16. The device of claim 1, wherein the photocatalyst is doped with one or more elements, the one or more elements comprising one or more of: iron, cobalt, chromium, gold, vanadium, manganese, carbon, boron, iodine, fluorine, sulfur, nitrogen or rare earth elements.

17. The device of claim 1, wherein the pattern of the one or more fiber optic light sources is arranged in a zig-zag pattern cross the fabric surface.

18. The device of claim 1, wherein the pattern allows the diffused part to hit every part of the fabric surface.

19. The device of claim 1, wherein the portion is constructed for repeated use by animals.

20. The device of claim 1, wherein the pattern of the one or more fiber optic light sources is chosen before the fabric is woven.

21. The device of claim 10, wherein the portion comprises a seat back of furniture, an armrest of furniture, or a seat cushion of furniture.

22. The device of claim 10, wherein the portion comprises a seat back of a chair within an interior of a car, an armrest of the chair within the interior of the car, or a seat cushion of the chair within the interior of the car.

23. The device of claim 10, wherein the portion comprises a seat cushion of a pet bed.

24. The device of claim 1, wherein the triggering mechanism comprises a pressure sensor, and wherein the pressure sensor is disposed under or behind the fabric surface.

* * * * *